United States Patent [19] [11] 3,937,739
de Radzitzky d'Ostrowick et al. [45] Feb. 10, 1976

[54] HYDROCARBON CONVERSION

[75] Inventors: Pierre M. J. G. de Radzitzky d'Ostrowick, Brussels; Philippe J. A. Camerman, Wezembeek-Oppem, both of Belgium

[73] Assignee: Labofina S. A., Brussels, Belgium

[22] Filed: June 19, 1973

[21] Appl. No.: 371,398

[30] Foreign Application Priority Data
May 4, 1973  Belgium ................ 130730

[52] U.S. Cl. .................. 260/604 R; 260/610 B
[51] Int. Cl.² .............................. C07C 45/02
[58] Field of Search ............ 260/604 R, 610 B

[56] References Cited
UNITED STATES PATENTS
2,683,751  7/1954  Filar ............................. 260/610 B
2,798,096  7/1957  Baumgartner .................. 260/610 B
3,442,954  5/1969  Crocker et al. ................ 260/592

FOREIGN PATENTS OR APPLICATIONS
1,139,172  1/1969  United Kingdom ............ 260/604 R
1,366,078  6/1964  France ......................... 260/604 R OTHER PUBLICATIONS
Maslennikon et al., Chemical Abstracts, Vol. 66, Col. item 75430m, 1967.
Oberright et al., Chem. Abstracts, Vol. 53, Col. 14487, 1959.

Primary Examiner—James O. Thomas, Jr.
Assistant Examiner—R. H. Liles

[57] ABSTRACT

A process for the oxidation of a diethylbenzene feed which comprises passing a molecular oxygen containing gas into contact with said feed at a temperature between 100° and 180°C in the presence of a superbasic sulfonate of an alkaline-earth metal in an amount within the range of 0.01 to 5% by weight of the diethylbenzene feed.

11 Claims, No Drawings

HYDROCARBON CONVERSION

BACKGROUND OF THE INVENTION

The present invention relates to a process for the conversion of hydrocarbons. More particularly, the present invention relates to the liquid phase conversion of diethylbenzenes by oxidation into diethylbenzene hydroperoxides.

U.S. Patent application Ser. No. 334,084, filed on Feb. 20, 1973 now U.S. Pat. No. 3,923,909, discloses a two-step process for producing ethylphenols and acetaldehyde via the liquid phase oxidation of diethylbenzenes. This process has as the first step the oxidation of diethylbenzene into diethylbenzene hydroperoxide which is then decomposed in the second step into ethylphenol and acetaldehyde, according to the following reactions:

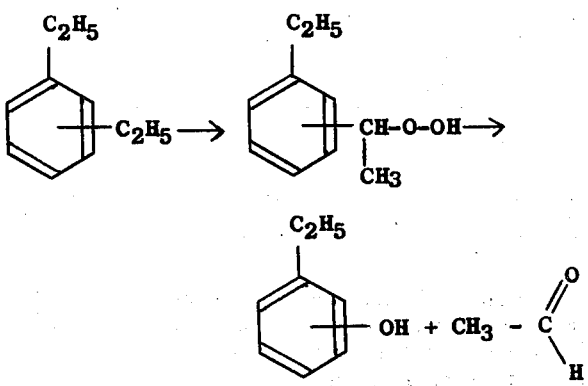

The first step is the most critical, the overall yield of the process and the rate of production of ethylphenols depending upon the selectivity of the oxidation for the production of the monohydroperoxide and on the rate of this oxidation.

An object of the present invention is to provide an improved process for the production of diethylbenzene hydroperoxides from diethylbenzenes.

Another object of the present invention is to provide a process for the selective oxidation of diethylbenzenes into corresponding monohydroperoxides.

A further object of the present invention is to provide an improved reaction rate for the oxidation of diethylbenzenes to the corresponding diethylbenzene hydroperoxide.

It is a further object of the present invention to provide a process for the oxidation of diethylbenzenes without the possibility of the danger of explosion when the oxidation is carried out in the presence of reactors constructed of iron or stainless steel.

According to the present invention, the process for producing diethylbenzene monohydroperoxides comprises the oxidation of a diethylbenzene feed by passing molecular oxygen containing gas into contact with said diethylbenzene at a temperature between 100° and 180°C in the presence of a superbasic sulfonate of alkaline earth metal in an amount corresponding to 0.01 to 5% by weight of the diethylbenzene feed.

The feed used in the process of the present invention may be a mixture of diethylbenzene isomers or either one of the isomers alone. In a particularly useful embodiment of the present invention, the feed consists of meta-diethylbenzene, the corresponding monohydroperoxide being then decomposed into m-ethylphenol which is itself a particularly useful compound.

In order to obtain high selectivity in hydroperoxides, the diethylbenzene feed must be of good purity and, in particular, the diethylbenzene should be free from acids and arylvinyl compounds. Also, in the event unreacted diethylbenzene is recycled, it is preferred to avoid a concentration of diethylbenzene oxidation products, other than hydroperoxides, higher than about 0.5% in the diethylbenzene feed. When this condition is fulfilled, most of the unconverted diethylbenzene recovered from the process of the present invention may be recycled without purication. However, in some instances, the recycled diethylbenzene may contain formic acid and ethylstyrene. These contaminants preferably are removed before the diethylbenzene is recycled.

The oxidation reaction of the diethylbenzene feed is carried out at a temperature which may vary from about 100° to 180°C. The oxidation rate of diethylbenzene increases as the reaction temperature is increased and, in order to minimize equipment sizes, it is desirable to carry out the reaction at the higher temperatures. However, the rates of formation of undesirable oxygenated by-products and the dangers of uncontrolled decomposition are also increased, as the reaction temperature is increased. Consequently, the reaction temperature during the oxidation step of the present process is generally maintained between about 125° and 160°C and more particularly between 130° and 150°C. According to a preferred embodiment of this invention, the oxidation is carried out by starting the reaction at about 150°C and then progressively decreasing the temperature down to about 140°C.

The oxidizing agent may be air, oxygen or other molecular oxygen containing gas. Air has the advantage of lower cost and generally, the mixtures of air and diethylbenzene which are suitable to perform the oxidation are outside the limits of explosion. The oxidation reaction may be carried out at atmospheric pressure or at somewhat higher pressures. However, the results of comparative experiments have shown that pressures higher than 10 atm. do not result in improved yields. Therefore, generally, pressures lower than 10 atm. are employed. Diethylbenzene is more preferably oxidized at atmospheric pressure.

The oxidation reaction is carried out by passing the molecular oxygen containing gas into liquid diethylbenzene under conditions insuring a rapid and intimate contact between the two phases, for example by using a bubble-column or a reactor with a stirring device. In order to avoid an excessive formation of undesirable by-products, more particularly of acid compounds which catalyze the decomposition of the formed hydroperoxide, it is desirable to use the oxygen containing gas in controlled amounts. A large excess of oxygen is detrimental with respect to the selectivity of the process. For this reason, the amount of oxygen in the vent gas from the reaction is kept preferably below 20% and more particularly below 10%. Moreover, vent gases containing less than 20% of oxygen are outside the explosion limits.

The oxidation reaction proceeds according to a chain mechanism with free radicals as chain propagators; therefore, it may be desirable to initiate this mechanism by means other than thermal self-initiation. Suitable initiators include peroxy compounds, such as perbenzoates, t.butylperoxide, diethylbenzene hydroperoxides and diazo compounds, such as azobiscyclohexanenitrile, which are soluble in the feed and which decompose at the reaction temperature to produce initiating radicals. The amount of initiator depends largely on its efficiency at the chosen temperature but generally does not exceed 5% by weight based on the feed. At a temperature higher than 135°C, the thermal self initiation is sufficiently rapid without addition of an initiator.

The selectivity for the production of the diethylbenzene monohydroperoxide depends not only on the reaction conditions, the feed purity, the reaction vessel material, the presence of additives but also to a large extent, on the degree of conversion. This is due partly to a detrimental effect of the by-products obtained by the thermal decomposition of the hydroperoxides and which accumulate progressively. Also, the diethylbenzene monohydroperoxide is oxidized to an increasing extent into other hydroperoxidic compounds and mainly to bishydroperoxide and acetyl-ethylbenzene hydroperoxide. Therefore, it is preferred to limit the diethylbenzene conversion. It has been found that the most useful conversions lie between 5 and 30%, and more particularly between about 10 and 25%.

By-products are formed during the oxidation of diethylbenzene into the corresponding hydroperoxide and some of these by-products, namely the acid compounds, tend to decompose the hydroperoxide and corrode the reaction vessel. Therefore, in order to minimize these drawbacks in accordance with the present invention, basic substances are added to the reaction mixture. The basic substances which are the most used consist of carbonates of alkaline and alkaline-earth metals, oxides of alkaline-earth metals, soaps of alkaline metals, pyridine and their mixtures. It now has been unexpectedly found that superbasic sulfonates of alkaline-earth metals are particularly valuable substances. These sulfonates improve the selectivity and the oxidation rate of the feed into the corresponding hydroperoxide.

Superbasic sulfonates of alkaline-earth metals (sometimes called carbonated sulfonates) are compounds having the general composition $$R - Y - M - CO_3 - (M - CO_3)_x - M - SO_3R$$

where R is an organic radical, usually an aliphatic, alicyclic, aromatic or mixed-type hydrocarbon radical having at least 18 carbon atoms, Y is $CO_3$ or $SO_3$ radicals, M is Ba, Ca or Mg and $x$ is an integer having a value in the range of 0 to 8. These superbasic sulfonate compounds are prepared by known processes. For example, calcium superbasic alkylbenzenenasulfonate may be prepared by adding a hydrocarbon solution of alkylbenzenesulfonic acid to a methanolic solution of calcium methylate and then introducing $CO_2$. Methanol is evaporated and the insoluble materials are recovered by filtration or centrifuging. The insoluble materials can be obtained in powder form by removing the hydrocarbon, for instance by spray drying.

The effects of the addition of the superbasic sulfonates on the oxidation rate in hydroperoxide and on the selectivity of the reaction are shown by the results of the following described comparative experiments in which m-diethylbenzene has been oxidized in batch operations. These experiments were carried out in a glass reactor, at a temperature of about 130°C, with oxygen as oxidizing gas at 1 atm. and in the presence of diethylbenzene hydroperoxide as initiator. For the sake of brevity, DEB is used for diethylbenzene and DEBOOH for the monohydroperoxide of DEB.

TABLE I.

| Experiment | 1 | 2 | 3 | 4 | 5 | 6 |
|---|---|---|---|---|---|---|
| Base | — | — | $Na_2CO_3$ | Ca sulfonate (b) | Ca sulfonate (b) | Mg sulfonate (b) |
| wt. % (a) | — | — | 1 | 1 | 1 | 1 |
| Oxidizing gas | | dry | wet | dry | dry | dry |
| Reaction time (minutes) | 260 | 400 | 240 | 160 | 240 | 250 |
| m-DEB conversion (%) | 15.5 | 20.0 | 15.0 | 15.7 | 21.1 | 19.3 |
| Selectivity in m-DEBOOH | 77.5 | 68.7 | 80.8 | 78.2 | 73.9 | 70.8 |

(a) weight % on a dry basis
(b) Ca and Mg salts of carbonated (heavy alkyl) benzene sulfonic acids.

The results set forth in Table I illustrate that the oxidation rate is noticeably increased, and the selectivity is improved, when the reaction is carried out in the presence of a superbasic sulfonate, more particularly calcium superbasic sulfonate. This effect is unexpected since the oxidation rate of other alkylbenzenes such as ethylbenzene and cumene is not increased and is even decreased when the oxidation is carried out in the presence of calcium superbasic sulfonate. Moreover, in such instances, the selectivity of the reaction is lower. The following Table II presents the results of comparative experiments with ethylbenzene and cumene.

TABLE II.

| Experiment | 7 | 8 | 9 | 10 |
|---|---|---|---|---|
| Hydrocarbon | Ethylbenzene | | Cumene | |
| Base | — | Ca sulfonate | — | Ca sulfonate |
| weight % | — | 1 | — | 1 |
| Oxidizing gas | dry | dry | dry | dry |
| Reaction time (minutes) | 345 | 345 | 205 | 240 |
| Hydrocarbon conversion (%) | 11.8 | 12.4 | 20.4 | 20.0 |
| Selectivity in monohydroperoxide | 82.5 | 64.2 | 93.8 | 86.0 |

The superbasic sulfonates of alkalino-earth metals are used in amounts which may vary within large limits, generally between 0.01 and 5% and more particularly between 0.01 and 2% by weight, based on the feed material. These amounts are calculated for superbasic sulfonates in powder form, it being understood that these substances may be used in a diluted form. The most advantageous concentration of sulfonates depends on the reaction conditions, particularly on the reaction temperature, on the oxidizing gas and its concentration and on the reactor materials of construction. The higher concentrations of sulfonates are generally used when the reaction is carried out at low temperature, with a high concentration of oxidizing gas and in a reactor made of an easily oxidizable material.

The oxidation of a diethylbenzene feed into the corresponding monohydroperoxide according to the present invention may be carried out in a reaction vessel which has internal surfaces made of iron or stainless steel without danger of explosion. Contrary to other basic substances such as carbonates, the superbasic sulfonates of alkalino-earth metals appear to act as passivating agents. Expensive materials such as titanium or silver or silver alloys are not required for the manufacture of the reactors used in accordance with the process of the present invention.

The features and other characteristics of the process of the present invention will be further described by the following non-limiting examples.

EXAMPLE 1

Distilled meta-diethylbenzene (m-DEB) (235 ml) was charged to a glass reactor equipped with a stirring device, a cooling system and a Dean and Stark condenser. Calcium salt of carbonated kerylbenzenesulfonic acid (0.17 wt. % calculated on the weitht of m-DEB) was then added. Air was bubbled into the liquid mixture with agitation at a rate of 34 liters per hour. The reaction mass was then heated to 150°C at which temperature oxygen uptake began rapidly. After about 20 minutes the oxygen percentage in the vent gas was depressed to about 9 to 10% and remained at this value throughout the course of the reaction. The temperature was progressively decreased as the m-DEB conversion increased in such a way that 140°C was reached when 22% conversion was obtained as determined by oxygen absorption measurements. This conversion was obtained after 130 minutes and the reaction mixture was then rapidly cooled to 30°–40°C and collected.

During the reaction some m-DEB (about 1% of the charged hydrocarbon) was collected in the condenser together with small amounts of water and formic acid. This m-DEB could be recycled to the oxidation reaction after washing with water.

The reaction mixture contained 22.2% by weight of total m-diethylbenzene hydroperoxides, which corresponds to a yield of 84.9% calculated on the reacted m-DEB. The content of monohydroperoxide in the total hydroperoxides amounted to 93.5%, corresponding to a yield of 79.4% calculated on the reacted m-DEB.

EXAMPLE 2

Experiments have been carried out in a titanium reactor with addition of superbasic calcium sulfonate to the starting m-DEB. Different concentrations of the sulfonate were used, at 140°C, ranging from 0.01 to 1% by weight in order to optimize the selectivity. It was found that selectivity is improved even with an amount of sulfonate as low as 0.01% and does not vary widely when this concentration is increased. In fact, the molar selectivities into total hydroperoxides obtained range between 78.7% and 80.3% at 22% DEB conversion. By way of comparison, similar experiments have been carried out in the absence of sulfonate. The molar selectivities were about 72%. The use of concentrations of calcium sulfonate higher than 0.1% is to improve the reaction rate. The reaction time is decreased by a factor 1.8 when using 1% instead of 0.1% of calcium sulfonate.

EXAMPLE 3

Oxidation of commercial DEB (mixture of the three isomers) has been carried out in a 316 stainless steel autoclave, at 150°–140°C, in the presence of 0.2 wt. % of powdered Ba superbasic sulfonate and with an air flow rate of about 154 liters per hour per liter of DEB. A 23% conversion was obtained in about 85 minutes. The selectivity was 84.85 mole % into total hydroperoxides and 78—79% into DEBOOH.

What is claimed is:

1. A process for the oxidation of a diethylbenzene feed to form diethylbenzene hydroperoxide which comprises passing a molecular oxygen containing gas into contact with said feed at a temperature between 100° and 180°C. in the presence of 0.01 to 5.0%, by weight, of said diethylbenzene feed, of a superbasic sulfonate of an alkaline earth metal of the formula:

$$R - Y - M - CO_3 - (M - CO_3)_x - M - SO_3R$$

wherein R is a hydrocarbon radical having at least 18 carbon atoms, Y is selected from the group consisting of $CO_3$ and $SO_3$ radicals, M is selected from the group consisting of barium, calcium and magnesium, and X is an integer between 0 and 8.

2. The process of claim 1 wherein the oxidation is carried out at a temperature of between 125° and 160°C.

3. The process of claim 1 wherein said superbasic sulfonate is a calcium sulfonate.

4. The process of claim 1 wherein said superbasic sulfonate is barium sulfonate.

5. The process of claim 1 wherein said superbasic sulfonate is magnesium sulfonate.

6. The process of claim 1 wherein the amount of superbasic sulfonate is within the range of 0.01 to 2% by weight, based on the feed material.

7. The process of claim 1 wherein the superbasic sulfonate is selected from the group consisting of the superbasic sulfonates of calcium, barium and magnesium, and is used in an amount of between 0.01 and 2% by weight based on the feed.

8. The process of claim 1, wherein said oxidation reaction is carried out in the presence of a free radical-producing initiator.

9. The process of claim 8, wherein said free radical initiators selected from the group consisting of a peroxy compound and a diazo compound.

10. A process for the production of ethyl phenol and acetaldehyde from a diethyl benzene feed which comprises passing a molecular oxygen containing gas into contact with said feed at a temperature between 100° and 180°C. in the presence of 0.01 to 5.0%, by weight, of said diethyl benzene feed, of a superbasic sulfonate of an alkaline earth metal of the formula:

$$R - Y - M - CO_3 - (M - CO_3)_x - M - SO_3R$$

wherein R is a hydrocarbon radical having at least 18 carbon atoms, Y is selected from the group consisting of $CO_3$ and $SO_3$ radicals, M is selected from the group consisting of barium, calcium and magnesium, and X is an integer between 0 and 8.

11. The process of claim 1, wherein said superbasic sulfonate of an alkaline earth metal is calcium superbasic alkylbenzenesulfonate.

* * * * *